United States Patent [19]
Tedder et al.

[11] Patent Number: 5,849,589
[45] Date of Patent: Dec. 15, 1998

[54] CULTURING MONOCYTES WITH IL-4, TNF-α AND GM-CSF TO INDUCE DIFFERENTIATION TO DENDRIC CELLS

[75] Inventors: Thomas F. Tedder, Durham, N.C.; Liang-Ji Zhou, Houston, Tex.

[73] Assignee: Duke University, Durham, N.C.

[21] Appl. No.: 613,310

[22] Filed: Mar. 11, 1996

[51] Int. Cl.$^6$ .............................. C12N 5/00; A01N 63/00
[52] U.S. Cl. .................. 435/377; 424/93.71; 435/375
[58] Field of Search ................................ 435/375, 377; 424/93.71

[56] References Cited

U.S. PATENT DOCUMENTS

| | | | |
|---|---|---|---|
| 4,845,653 | 7/1989 | Conrad et al. | 364/521 |
| 5,316,920 | 5/1994 | Tedder et al. | 435/69.3 |
| 5,648,219 | 7/1997 | MacKay et al. | 435/6 |

FOREIGN PATENT DOCUMENTS

| | | |
|---|---|---|
| WO 93/20185 | 10/1993 | WIPO . |
| WO 94/02156 | 2/1994 | WIPO . |
| WO 94/28113 | 12/1994 | WIPO . |
| WO 95/12409 | 5/1995 | WIPO . |

OTHER PUBLICATIONS

Morse et al., "CD83 is a marker for mature dentritic cells generated from peripheral blood mononuclear cells", 37th Annual Meeting of the Americal Society of Hematology, Blood 86 (10 Suppl. 1): 323a (1995).
Zhou et al., "CD83 is a marker for mature dendritic cells generated from peripheral blood mononuclear cells", 37th Annual Metting of the American Society of Hematology, Blood 86 (10 Suppl. 1):323! (1995).
Cameron et al., Science 257:383–387 (1992).
Cameron et al., Clin. Exp. Immunol. 88:226–236 (1992).
Caux et al., Nature 360:258–261 (1992).
Caux et al., Immunology Today 16:2–4 (1995).
Clare–Salzler et al., J. Clin. Invest. 90:741–748 (1992).
Egner et al., Transplantation Proc. 24:2318 (1992).
Egner et al., Transplantation 56:945–950 (1993).
CD83 Workshop Report, Engel, P., Wagner, N. and Tedder, T.F., eds., Oxford University Press, Oxford, vol. 1, pp. 693–695 (1995).
Freudenthal et al., Proc. Natl. Acad. Sci. USA 87:7698–7702 (1990).
Grage–Griebenow et al., Eur. J. Immunol 23:3126–3135 (1993).
Inaba et al., J. Exp. Med. 175:1157–1167 (1992).
Inaba et al., J. Exp. Med. 176:1693–1702 (1992).
Inaba et al., J. Exp. Med. 178:479–488 (1993).
Inaba et al., Proc. Natl. Acad. Sci. USA 90:3038–3042 (1993).
Kabel et al., Immunobiol. 179:395–411 (1989).
Kasinrerk et al., J. Immunol 150:579–584 (1993).
Knight et al., Immunology 57:595–603 (1986).
Knight et al., J. Invest. Dermatol. Supplement 99:33S–38S (1992).
Kuntz–Crow et al., Clin. Exp. Immunol. 49:338–346 (1982).
Langhoff et al., J. Invest. Dermatol. 99:89S–94S (1992).
Langhoff et al., J. Clin. Invest. 91:2721–2726 (1993).
Levine et al., Proc. Natl. Acad. Sci. USA 89:8342–8346 (1992).
Najar et al., Eur. J. Immunol. 51:339–346 (1990).
Nestle et al., J. Immunol. 151:6535–6545 (1993).
O'Doherty et al., J. Exp. Med. 178:1067–1078 (1993).
O'Doherty et al., Immunol. 82:487–493 (1994).
Patterson et al., J. Gen. Virol. 76:1155–1163 (1995).
Peters et al., Pathobiol. 59:122–126 (1991).
Pinchuk et al., Immunity 1:317–325 (1994).
Pope et al., Cell 78:389–398 (1994).
Reid et al., Blood 76:1139–1149 (1990).
Reid et al., J. Immunol. 149:2681–2688 (1992).
Romani et al., J. Exp. Med. 180:83–93 (1994).
Ruppert et al., Immunobiology 182:449–464 (1991).
Sallusto et al., J. Exp. Med. 179:1109–1118 (1994).
Santiago–Schwarz et al., J. Leukoc. Biol. 52:274–281 (1992).
Santiago–Schwarz et al., Blood 82:3019–3028 (1993).
Steinman et al., J. Exp. Med. 157:613–627 (1983).
Steinman et al., Annu. Rev. Immunol. 9:271–296 (1991).
Stingl and Bergstresser, Immunology Today 16:330–333 (1995).
Szabolcs et al., J. Immunol. 154:5851–5861 (1995).
Thomas et al., J. Immunol. 150:821–834 (1993).
Van Voorhis et al., J. Exp. Med. 155:1172–1187 (1982).
Weissman et al., Proc. Natl. Acad. Sci. USA 92:826–830 (1995).
Wood et al., Ameri. J. Path. 141:789–795 (1992).
Xu et al., Scand. J. Immunol. 36:689–696 (1992).
Young et al., Cell. Immunol. 111:167–182 (1988).
Young et al., J. Exp. Med. 171:1315–1332 (1990).
Zhou et al., Blood 86:3295–3301 (1995).
Zhou et al., J. of Immunol. 149:735–742 (1992).
Zhou and Tedder, J. of Immunol. 154:3821–3835 (1995).
Ziegler et al., J. of Autoimmunity 5:571–579 (1992).

*Primary Examiner*—Sandra E. Saucier
*Attorney, Agent, or Firm*—Fish & Richardson P.C.

[57] ABSTRACT

Disclosed is a method for inducing the differentiation of a monocyte into a dendritic cell, the method including the culturing of a monocyte in a medium including GM-CSF, IL-4, and TNF-α.

22 Claims, 7 Drawing Sheets

CULTURING MONOCYTES WITH IL-4, TNF-α AND GM-CSF TO INDUCE DIFFERENTIATION TO DENDRIC CELLS

STATEMENT AS TO FEDERALLY SPONSORED RESEARCH

This invention was made in part with Government funding and the Government therefore has certain rights in the invention.

BACKGROUND OF THE INVENTION

This invention relates to methods and compositions for the growth and differentiation of mammalian cells, particularly the growth and differentiation of monocyte-derived dendritic cells.

Dendritic cells are said to be potent antigen presenting cells (APCS) in the immune system and to be critically involved in the initiation of primary immune responses, autoimmune diseases, graft rejection, human immunodeficiency virus infection, and the generation of T cell-dependent antibodies (Steinman, *Annu. Rev. Immunol.* 9: 271–296, 1991). Mature dendritic cells are also the principal stimulatory cells of primary mixed leukocyte reactions (Steinman et al., *J. Exp. Med.* 157: 613, 1982; Kuntz Crow et al, *Clin. Exp. Immunol.* 49: 338, 1986). However, the study of dendritic cells has proven difficult because they represent only a small subpopulation of bone marrow-derived leukocytes which includes interdigitating reticulum cells in lymphoid organs, blood dendritic cells, Langerhans cells in the epidermis of the skin, and dermal dendritic cells (Steinman, 1991). In addition, dendritic cells have been primarily isolated and studied based on their unique morphology and lack of surface antigens when compared to T cells, B cells, monocytes, and NK cells.

Dendritic cells are found in all tissues and organs of the body. They have been primarily classified by their tissue location and include interdigitating reticulum cells in lymphoid organs, veiled cells in afferent lymph, blood dendritic cells in the circulation, Langerhans cells in the epidermis, and dermal dendritic cells in the dermis of the skin (Steinman, 1991; Steinman et al., *J. Exp. Med.* 137:1142–1162, 1973). Dendritic cells are also found in non-lymphoid organs such as the heart, lung, gut, and synovium (Steinman, supra, 1991). As it is not known whether the different dendritic cell populations represent various stages of maturation, delineation of the developmental pathways used by dendritic cells is of considerable importance.

SUMMARY OF THE INVENTION

We have discovered a novel method for culturing monocytes that results in the differentiation of dendritic cells.

In general, the invention features a method for inducing the differentiation of a monocyte into a dendritic cell, the method including culturing the monocyte in a medium including granulocyte/macrophage-colony stimulating factor (GM-CSF), interleukin-4 (IL-4), and tumor necrosis factor-α (TNF-α). In other preferred embodiments, the method involves first culturing the monocyte in a medium including GM-CSF and IL-4, and then adding TNF-α to the GM-CSF and IL-4 medium.

In preferred embodiments, the monocyte is a plastic-adherent human blood monocyte (e.g., a $CD14^+$ and $CD1a^-$ monocyte) and the dendritic cell is a human dendritic cell (e.g., a $CD83^+$ dendritic cell) which is capable of inducing T cell proliferation.

In other embodiments, the method involves maintaining GM-CSF concentration in the medium in the range of about 125–2,000 U/ml, IL-4 concentration in the range of about 1–500 U/ml, and TNF-α concentration in the range of about 50–50,000 U/ml. Preferably, the GM-CSF concentration in the medium is about 800 U/ml, IL-4 concentration is about 500 U/ml, and TNF-α concentration is about 100 U/ml. One unit (1 U) of GM-CSF is defined as the amount of GM-CSF required to support half-maximal $^3$H-TdR incorporation by TF-1 cells; one unit (1 U) of IL-4 is defined as the amount of IL-4 required to induce half-maximal $^3$H-TdR incorporation by peripheral blood lymphocytes; and one unit (1 U) of TNF-α is defined as the amount of TNF-α required to mediate half-maximal cytotoxicity of L929 cells.

In other preferred embodiments, the method includes administering the dendritic cell which is produced according to the above methods to a mammal, e.g., for ex vivo cell transplantation therapy.

In another aspect, the invention features a composition for inducing the differentiation of a monocyte into a dendritic cell, the composition including GM-CSF, IL-4, and TNF-α at concentrations of between about 125–2,000 U/ml, 1–500 U/ml, and 50–50,000 U/ml, respectively. In preferred embodiments, the composition includes GM-CSF, IL-4, and TNF-α at concentrations of between about 500–1,000 U/ml, 250–500 U/ml, and 100–1,000 U/ml, respectively. Preferably, the GM-CSF concentration in the composition is about 800 U/ml, IL-4 concentration is about 500 U/ml, and TNF-α concentration is about 100 U/ml.

In another aspect, the invention features a population of dendritic cells including greater than 50% $CD83^+$ dendritic cells produced according to the method described above. In other preferred embodiments, the population of dendritic cells is at least 60% $CD83^+$ dendritic cells, preferably greater than 70%, and more preferably greater than 85% or 95% $CD83^+$ dendritic cells.

In another aspect, the invention features a method for generating a population of dendritic cells, the method involving (a) inducing the differentiation of a population of monocytes into a population of dendritic cells, by culturing the population of monocytes in a medium including GM-CSF, IL-4, and TNF-α; and (b) recovering the population of dendritic cells. In other preferred embodiments, the method involves first culturing the population of monocytes in a medium including GM-CSF and IL-4, and then adding TNF-α to the GM-CSF and IL-4 medium.

In preferred embodiments, the monocyte is a plastic-adherent human blood monocyte (e.g., a $CD14^+$ and $CD1a^-$ monocyte) and the dendritic cell is a mature human dendritic cell (e.g., a $CD83^+$ dendritic cell) which is capable of inducing T cell proliferation.

In preferred embodiments, recovery of the population of dendritic cells includes flow cytometry or cell isolation methods.

In another aspect, the invention features a method for increasing the number of dendritic cells in a human, the method including administering a therapeutically effective amount of a composition including GM-CSF, IL-4, and TNF-α. In other preferred embodiments, the method involves first administering a composition of GM-CSF and IL-4, and then adding TNF-α. For example, the TNF-α is added to a GM-CSF and IL-4 composition after a period of about 5 days.

By "dendritic cell" is meant a cell of lymphoid or non-lymphoid origin that expresses CD83 as described by Zhou et al. (*J. Immunol.* 154: 3821–3835, 1995). Dendritic cells are also capable of expressing high levels of MHC class I and II products, and initiating a mixed leukocyte reaction (as described herein). In addition, dendritic cells lack a number of myeloid markers including, without limitation, $CD14^-$ and CD86. Furthermore, dendritic cells are motile, and are capable of efficiently clustering and activating T cells (e.g., such cells are capable of expanding $CD4^+$ T cells).

Dendritic cells may now be produced in large quantities. For example, the methods described herein allow for the simple and rapid differentiation of dendritic cells from plastic-adherent human blood monocytes. In addition, the methods of the invention are straightforward to perform, thereby enabling the purification of large populations of dendritic cells. Furthermore, the methods of the invention disclosed herein provide for the production of clinically useful populations of dendritic cells, which are useful, for example, in the prevention and treatment of disease and for the preparation of new therapeutic antigens.

Unless otherwise defined, all technical terms and scientific terms used herein have the same meaning as commonly understood by one of ordinary skill in the art to which the invention belongs.

Other features and advantages of the invention will be apparent from the following detailed description and from the claims.

DETAILED DESCRIPTION

The drawings will first be described.
Drawings

FIG. 1A shows the differentiation of $CD14^+$ blood monocytes which were cultured with the indicated combinations of cytokines and their cell surface phenotype as examined by two-color immunofluorescence analysis over a 12 day incubation period. Results are representative of those obtained in 13 independent experiments. FIGS. 1B and 1C show the differentiation of $CD14^+$ blood monocytes which were cultured with GM-CSF and IL-4 for 5 days before the cultures were split and TNF-α was then added to the indicated cultures. The surface phenotype of cells was examined by two-color immunofluorescence analysis over the subsequent 7 days. Results from two independent assays are shown which are representative of those obtained in 10 experiments.

FIG. 2A is a photograph showing a phase-contrast image of $CD14^+$ monocytes which were cultured with cytokines for 2 days. FIGS. 2B and 2C are photographs showing the phase-contrast images of $CD14^+$ monocytes which were cultured with cytokines for 5 days. FIGS. 2D–2F are photographs of transmission electron microscopic images showing the ultrastructure of monocyte-derived $CD83^+$ cells isolated by cell sorting from 7 day cultures containing GM-CSF, IL-4, and TNF-α. FIG. 2G is a photograph of a transmission electron microscopic image of $CD14^+$ monocytes before cell culture. FIG. 2H is a photograph of a transmission electron microscopic image of blood $CD83^+$ dendritic cells. (Magnifications are as follows: FIGS. 2A–B, 200×; FIG. 2C, 400×; FIG. 2D, 1,855×; FIG. 2E–H, 5,800×).

FIG. 3 is a series of two-color immunofluorescence profiles showing the cell surface phenotype of monocyte-derived $CD83^+$ cells. $CD14^+$ monocytes were cultured in GM-CSF and IL-4 for 5 days with TNF-α added during the final 2 days of 7 day cultures. Each histogram is representative of results obtained with 2 to 10 different cell preparations and the figure is a compilation of results from multiple experiments. In all cases, similar flow cytometer settings were used to ensure uniformity, and the gates which delineated the histograms obtained from control cell populations stained with control antibodies are shown. The fluorescence intensity of $CD83^+$ cell expression of class II antigens exceeded the four decade log scale and therefore accumulates on the far right of the histogram.

FIG. 4A is a graph showing the AMLR using $CD14^+$ monocytes cultured for 7 days with GM-CSF and IL-4 (-o-) or GM-CSF, IL-4, and TNF-α (-■-) as stimulator cells. FIG. 4B is a graph showing the AMLR using $CD83^+$ (-■-) or $CD83^-$ (-□-) cells obtained from the GM-CSF, IL-4, and TNF-α cultures which were used as stimulator cells. Values are the mean cpm (±SD) obtained for triplicate cultures and are representative of those obtained in two experiments.

There now follows a description of the compositions and methods that are useful for promoting the differentiation of monocytes into dendritic cells. These examples are provided for the purpose of illustrating the invention, and should not be construed as limiting.

Cytokine-induced Monocyte Differentiation

To assess the effects of cytokines on the differentiation of monocytes, plastic-adherent $CD14^+$ $CD1a^-$ monocytes were purified from adult human blood and cultured with three different combinations of cytokines as follows.

Mononuclear cells were isolated by Ficoll-Paque (Pharmacia, Piscataway, N.J.) density gradient centrifugation of heparinized blood obtained from healthy adult donors according to standard protocols. The monocytes were then further purified using plastic adherence as described by Zhou et al. (*J. Immunology* 154:3821–3835, 1995). Isolated monocytes were subsequently recovered by incubating in cold saline for 20 minutes at 4° C., at which time monocytes were easily removed from the plates. The monocytes were then resuspended at $5 \times 10^6$ cells/ml and layered onto hypertonic 14.5% metrizamide (Sigma, St. Louis, Mo.) in 15 ml conical centrifuge tubes and centrifuged at 650×g for 15 minutes at room temperature to sediment contaminating lymphocytes. The monocytes (>98% $CD14^+$) were then harvested from the interface of the metrizamide gradient, resuspended in RPMI 1640 medium (Gibco-BRL, Gaithersberg, Md.) containing 10% fetal calf serum, 10 mM of glutamine, and penicillin/streptomycin, and plated into 6 well tissue culture plates ($1 \times 10^6$ cells/ml, 5–10 ml/well). Cytokines, GM-CSF (800 U/ml), IL-4 (500 U/ml), and TNF-α (100 U/ml) (from Genzyme, Cambridge, Mass.) were added to the cultures as indicated. The cultures were fed with fresh media and cytokines every three days, and cell differentiation was monitored by checking cellular morphology by light microscopy and by two-color immunofluorescence staining with flow cytometry analysis as described by Zhou et al. (supra).

Indirect immunofluorescence staining was carried out after washing the cells twice with culture medium as described by Zhou et al. (supra). Antibodies used included FITC-conjugated HB15a ($IgG_{2b}$), (Zhou et al., supra), phycoerythrin (PE)-conjugated CD14 (Coulter Corp., Miami, Fla.), and CD1a-PE (Coulter) and antibodies from the Fifth International Leukocyte Antigen Workshop. Appropriate isotype-matched nonspecific control monoclonal antibodies (Coulter) were used in all experiments to determine the levels of background staining. The labeled cells were then washed with saline containing 2% calf serum, and ten thousand cells were analyzed by flow cytometry using an Elite flow cytometer (Coulter).

Figure 1A:
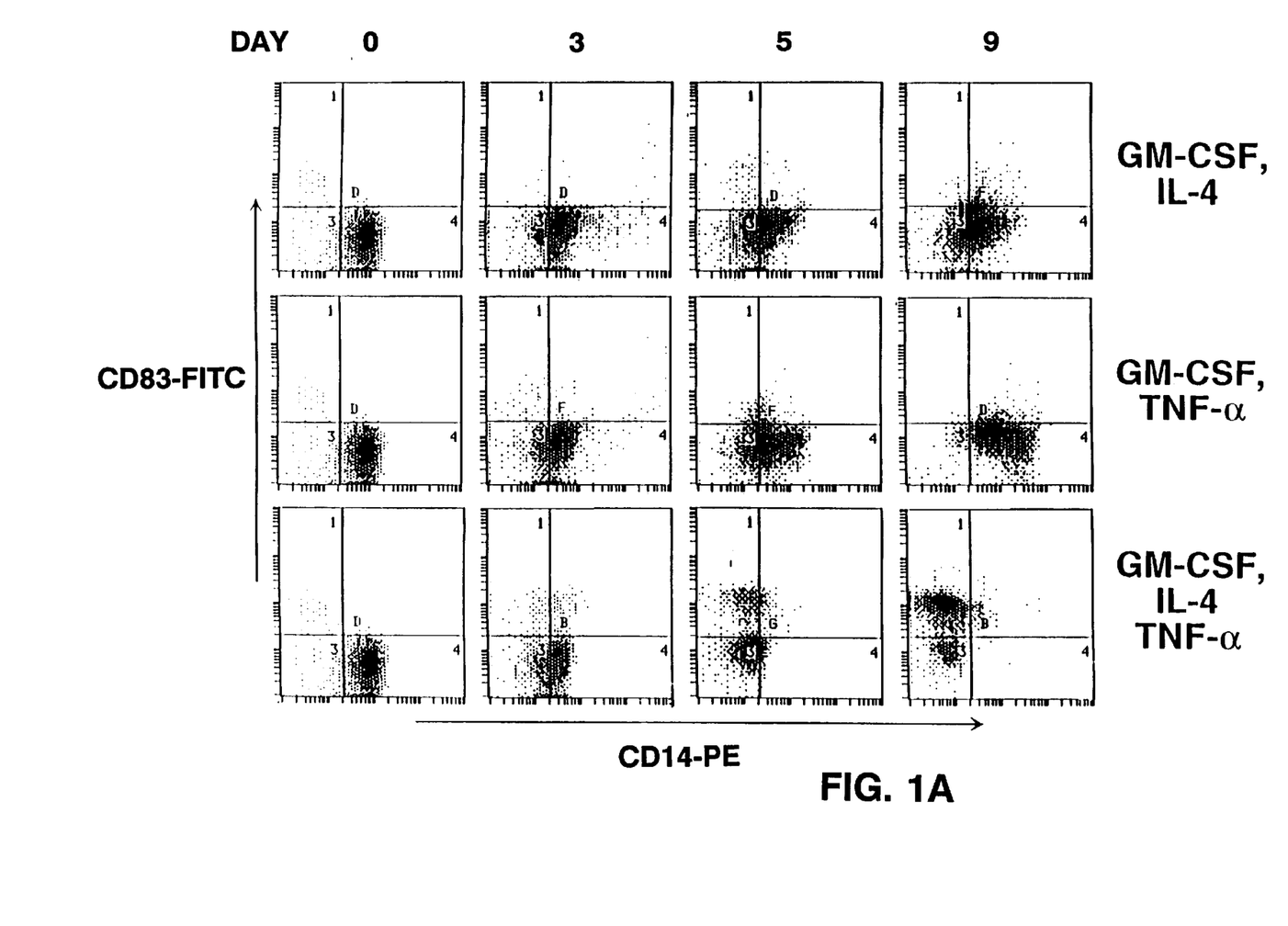
FIGS. 1A–C are a series of two-color immunofluorescence profiles showing the differentiation of monocytes cultured with GM-CSF, IL-4, and TNF-α into $CD83^+$ dendritic cells.
Figure 1B:
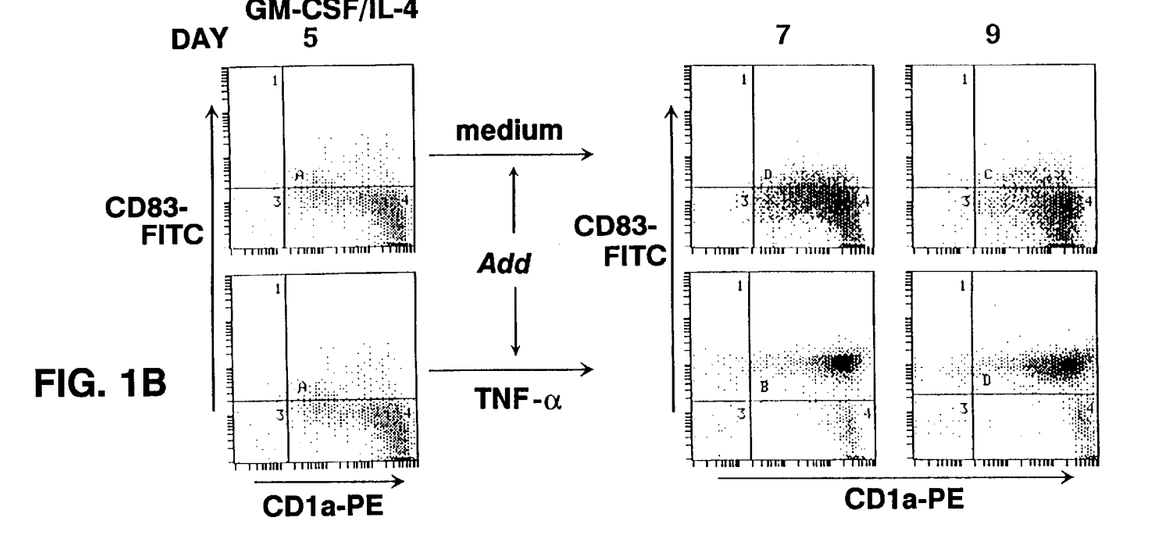

Monocytes cultured with GM-CSF and IL-4 generated small distinctive clusters of cells which formed on day two. With further culturing, these cellular clusters increased in size and were similar to those previously described for cultured blood dendritic cell precursors and $CD34^+$ cells from bone marrow. As shown in FIG. 1A, these cells remained $CD14^+$ and did not express CD83 at any time point, although they did become $CD1a^+$ (FIG. 1B). Monocytes cultured with GM-CSF and TNF-α primarily adhered to the tissue culture plates and only formed small loose cell clusters similar to those described for $CD34^+$ stem cells cultured with GM-CSF and TNF-α. Monocytes cultured with either GM-CSF and IL-4 or GM-CSF and TNF-α eventually became large, macrophage-like cells after 12 days of culture, but remained $CD14^+$ and $CD83^-$.

Figure 1C:
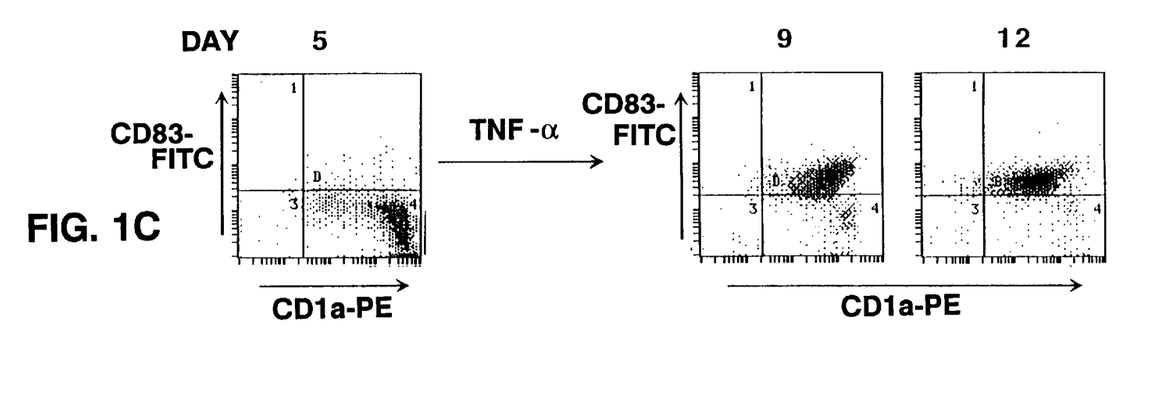
Figure 2A:
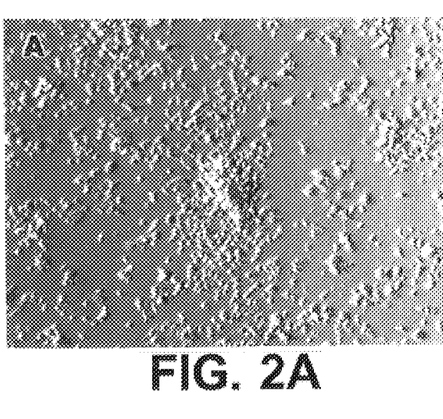
FIGS. 2A–H are a series of photographs showing the ultrastructural morphology of monocytes cultured with GM-CSF, IL-4, and TNF-α.
Figure 2B:
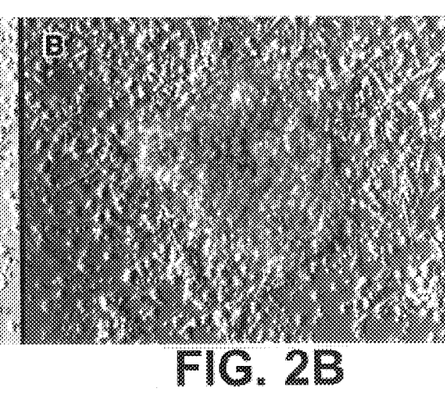
Figure 2C:
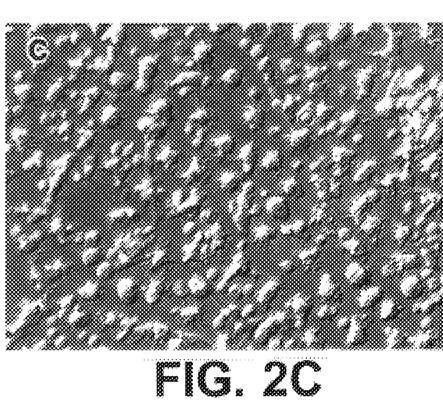

In contrast, monocytes cultured with GM-CSF, IL-4, and TNF-α generated small clusters of cells on day 2 which were semi-adherent to the tissue culture plates (FIG. 2A). The cells were tightly clustered together by day 5 (FIG. 2B) with some cells located between clusters (FIG. 2C). A large percentage (40–80%) of the monocytes differentiated into $CD83^+$ $CD14^-$ cells, but this usually required 10–12 days of culture (FIG. 1A). In contrast, if TNF-α was added to GM-CSF and IL-4 cultures at day five, the cells became adherent to the tissue culture plates and 78–95% of the cells became $CD83^+$ within 2–3 days (FIG. 1B). Additionally, these cells exhibited the characteristic cellular projections and motility of dendritic cells when examined by light microscopy (FIG. 2C), and continually extended, retracted, and reoriented their cellular processes and veils. Following acquisition of CD83 expression by cultured monocytes, there was a decrease in CD1a expression (FIG. 1C) which is typical of $CD83^+$ blood dendritic cells. Culturing monocytes continuously with GM-CSF, IL-4, and TNF-α also resulted in a large percentage (40–80%) of the cells becoming $CD83^+$, but this usually required 10–12 days of culture.

In all three of the above culture systems, cell viability consistently remained >95% as determined by trypan blue exclusion until day 14 to 15 when the cells appeared to increase in size and the cell clusters began to deteriorate. At day 20 or 21, the cells cultured with GM-CSF, IL-4, and TNF-α became large, round macrophage-like cells, despite the addition of fresh cytokines. Monocytes or $CD83^+$ dendritic cells isolated from blood did not expand in cell number or incorporate significant amounts of radiolabeled thymidine when cultured in the presence of cytokines. These results indicated that TNF-α-induced differentiation of blood monocytes cultured with GM-CSF and IL-4 generated dendritic-like cells within 7–9 days, with a yield of $CD83^+$ cells similar to the number of monocytes cultured.

Monocyte-Derived $CD83^+$ Cells Exhibit a Dendritic Cell Morphology

Monocyte-derived $CD83^+$ cells generated with GM-CSF, IL-4, and TNF-α were isolated using a fluorescence-based cell sorter and were cytocentrifuged onto glass slides to study their cellular morphology by phase-contrast microscopy. All of the monocyte-derived $CD83^+$ cells exhibited the characteristic cellular projections and mobility of dendritic cells (FIG. 2C), and continually extended, retracted and reoriented their cellular processes and veils.

In addition, ultrastructural aspects of cultured monocytes were examined by transmission electron microscopy as follows. $CD14^+$ monocytes were isolated as described above. $CD83^+$ cells were isolated from day 7 cultures of monocytes cultured with GM-CSF, IL-4, and TNF-α by fluorescence-based cell sorting using an Elite flow cytometer as described by Zhou et al. (supra). These cell preparations were found to be >99% $CD83^+$ when the isolated cells were re-examined for fluorescence staining. The cells were then pelleted by centrifugation and fixed with a 2% solution of glutaraldehyde in 150 mM of sodium cacodylate buffer containing 2.5 mM $CaCl_2$ (pH 7.2). The resulting cell pellet was washed with buffer and embedded in 1% agar. The pellet was postfixed for one hour on ice with 2% osmium tetroxide plus 1% of potassium ferrocyanide in the same buffer, washed with cacodylate buffer, and then washed with 200 mM Na-acetate (pH 5.2). The resulting sample was en bloc stained for one hour with 1% uranyl acetate in Na acetate buffer. After dehydration in ethanol, the pellet was infiltrated with and embedded in EMBED 812 (EM Sciences). Thin sections of 90 nm were cut on a Reichart Ultracut E microtome and stained with uranyl acetate, followed by Sato lead, washed, and examined in a Philips EM300 electron microscope.

Figure 2D:
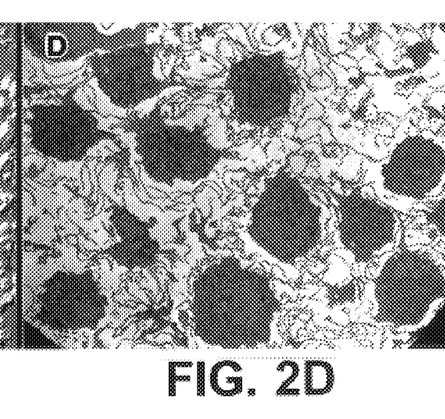
Figure 2E:
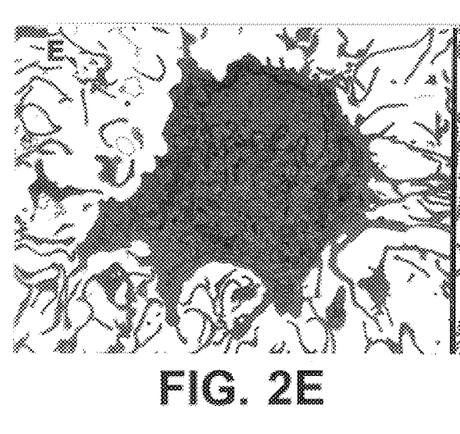
Figure 2F:
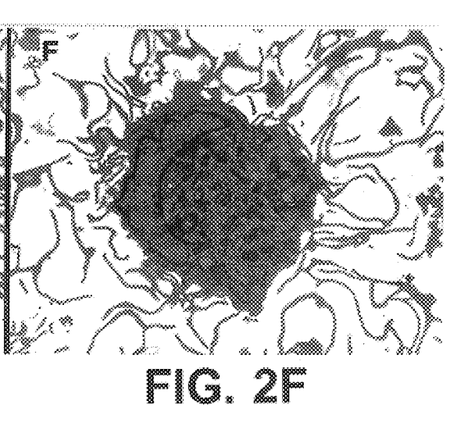
Figures 2G, 2H:
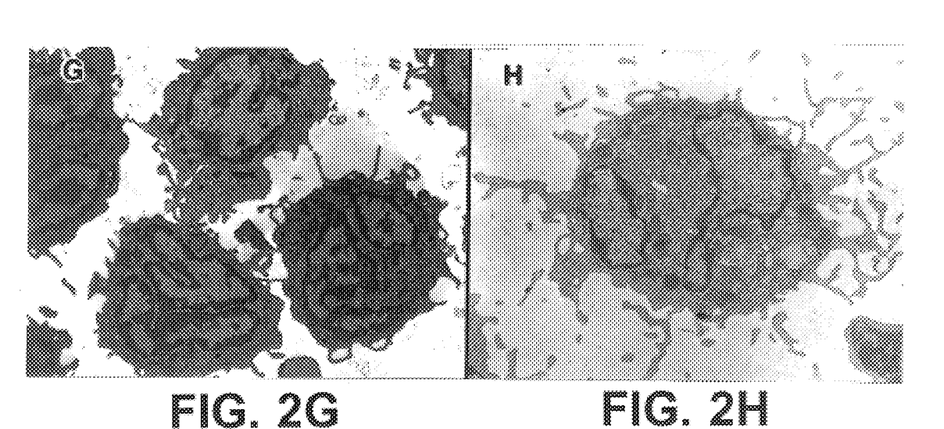

Transmission electron microscopy revealed that all of the $CD83^+$ cells were morphologically homogenous (FIG. 2D) with large irregular-shaped nuclei, numerous mitochondria, relatively few cytoplasmic granules and lysosomes, several vesicles, and obvious abundant cellular projections (FIGS. 2E–F). The morphology of monocyte-derived $CD83^+$ cells was identical to that of $CD83^+$ blood dendritic cells (FIG. 2H) and was quite distinct from that of monocytes (FIG. 2G).

Monocyte-Derived $CD83^+$ Cells Exhibit a Dendritic Cell Phenotype

The cell surface phenotype of monocyte-derived $CD83^+$ cells was examined as follows. $CD14^+$ monocytes cultured in GM-CSF, IL-4, and TNF-α for 7 days were examined by two-color immunofluorescence staining with flow cytometry analysis as described above. Isolated cells were then incubated for 20 minutes on ice with each test monoclonal antibody as either purified antibody or ascites fluid diluted for immunostaining. Test monoclonal antibodies were directly conjugated with phycoerythrin (PE) by the manufacturer, or were biotinylated. When biotinylated primary antibodies were used, staining was visualized using PE-conjugated streptavidin (Fisher Scientific, Pittsburgh, Pa.). Alternatively, the labeled cells were incubated with PE-conjugated goat anti-mouse Ig antibody (Fisher Scientific) for 20 minutes on ice. The cells were subsequently incubated with excess unlabeled mouse ascites fluid (to block all antibody binding sites) and incubated with FITC-conjugated HB15a monoclonal antibody.

Figure 3:
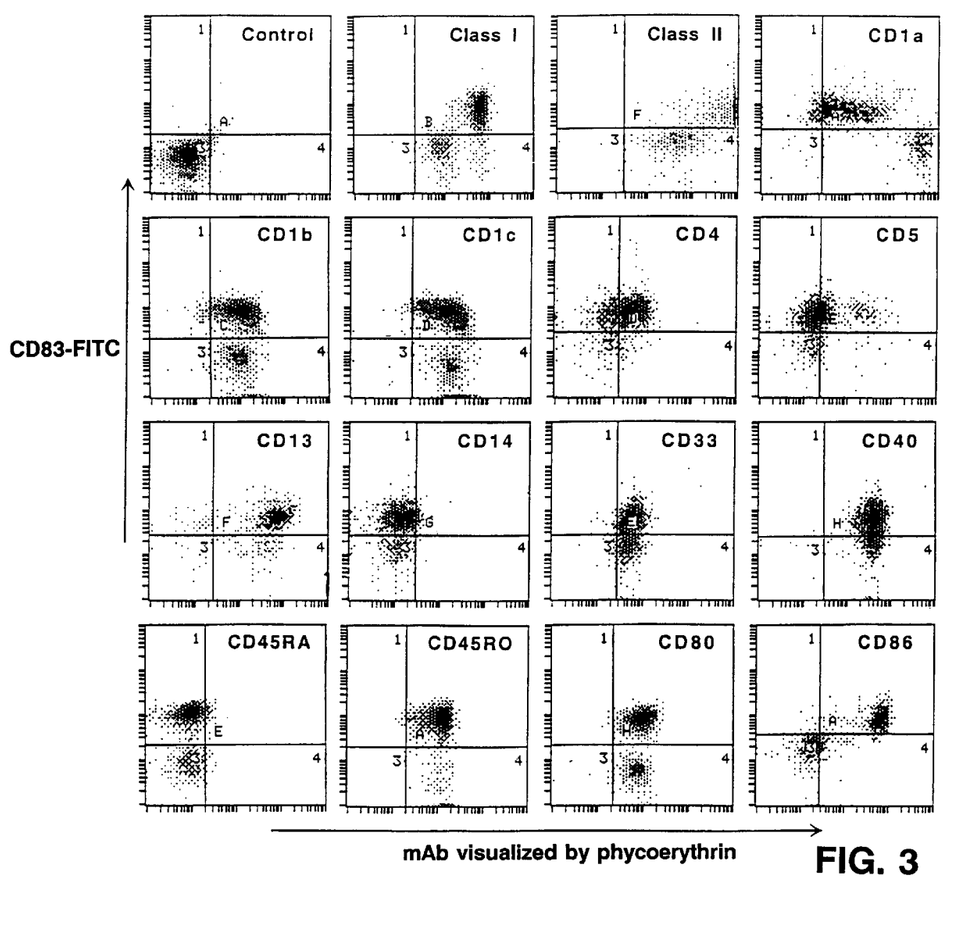

The phenotype of monocyte-derived $CD83^+$ cells was similar to that of $CD83^+$ dendritic cells isolated from blood. As shown in FIG. 3 and Table I (below), monocyte-derived $CD83^+$ cells expressed the CD13 and CD33 myeloid cell surface antigens, but lacked most other myeloid markers. In addition, cultured $CD83^+$ cells expressed CD1c, CD13, CD29, CD31, CD40, CD44, CD45RO, CD86, and high levels of MHC class I and class II molecules, as did blood $CD83^+$ dendritic cells. In contrast with blood $CD83^+$ dendritic cells, monocyte-derived $CD83^+$ cells expressed CD1a, CD1b, CD4, and CD80, but were negative or mostly negative for CD2, CD5, CD15s, CD25, α2,6-sialic acid, and CMRF-44. The phenotype of the $CD83^+$ cells was generally homogenous with all cells being either positive or negative for specific markers. However, small subpopulations of $CD83^+$ cells that lacked CD4, yet expressed CD2 and CD5 were observed in some cultures suggesting further differentiation of these cells. The phenotype of CD83⁻ cells was consistent with their macrophage-like morphology (FIG. 3). These results indicated that monocyte-derived CD83⁺ cells were closely related to dermal Langerhans cells, which expressed CD83 and CD1a.

indicate that the combination of GM-CSF, IL-4, and TNF-α induces optimal monocyte differentiation into functionally mature CD83⁺ dendritic cells.

The results of the experiments described herein demonstrated that CD83⁺ cells generated from blood CD14⁺ monocytes were a homogenous and unique population of cells

TABLE I

Surface Antigen Expression by Cell Populations

| Antigen | Antibody | Blood Monocytes | Differentiated CD83+ | Monocytes CD83− | CD83+ Blood DC |
|---|---|---|---|---|---|
| MHC class I | W6.32 | ++ | +++ | ++ | +++ |
| MHC class II | I3 | +++ | +++++ | +++ | ++++ |
| CD1a | T6 | − | ++ | ++++ | − |
| CD1b | 4A7.6.5 | − | ++ | ++ | − |
| CD1c | 10C3 | − | ++ | ++ | ++ |
| CD2 | T11 | − | +/−, few ++ | +/− | ++ |
| CD3 | T3 | − | − | +/− | − |
| CD4 | T4 | +/− | +/−, few − | + | − |
| CD5 | T1 | + | +/−, few ++ | +/− | +++ |
| CD13 | MY7 | ++ | +++ | +++ | ++ |
| CD14 | MY4 | ++ | − | − | − |
| CD15s | csLex | − | − | − | +++ |
| CD19 | B4 | − | − | − | − |
| CD20 | B1 | − | − | − | − |
| CD25 | IL-2R | − | −, few + | − | + |
| CD29 | 4B4 | ++ | ++ | ++ | ++ |
| CD31 | 1F11 | ++ | + | + | +/− |
| CD33 | MY9 | ++ | +, weak | + | ++ |
| CD40 | HB14 | + | ++ | ++ | + |
| CD45 | KC56 | ++ | + | + | + |
| CD45RA | 2H4 | − | − | − | − |
| CD45RO | UCHL-1 | − | ++ | ++ | ++ |
| CD54 | HAE-4a | − | +/− | +, weak | + |
| CD80 | B7-g, BB1 | − | + | + | + |
| CD86 | FUN-1 | +/− | +++ | − | +++ |
| α2,6 sialic acid | HB6 | − | − | − | ++ |
| CMRF-44 | | − | − | − | + |

DC, dendritic cells. The methods and levels of surface antigen staining are as described in FIG. 3. Results indicate: −, no staining above background levels; +/−, variable weak reactivity; + to +++++, increasingly positive staining based on a relative linear scale.

Stimulating Activity of CD83⁺ Cells in Mixed Leukocyte Reactions

Because the induction of a potent mixed leukocyte reaction is a characteristic feature of mature dendritic cells, the ability of monocyte-derived CD83⁺ cells to induce the proliferation of allogeneic T cells was examined as follows. CD14⁺ monocytes were cultured as described above. Monocyte-derived CD83⁺ and CD83⁻ cells were isolated by cell sorting as above. Responder T cells used for allogeneic mixed leukocyte reaction (AMLR) assays were isolated by sheep erythrocyte rosetting of mononuclear cells obtained from healthy donors according to standard methods. AMLR assays were carried out as described by Freudenthal and Steinman (*Proc. Natl. Acad. Sci. USA* 87: 7689–7702, 1990).

Figure 4A:
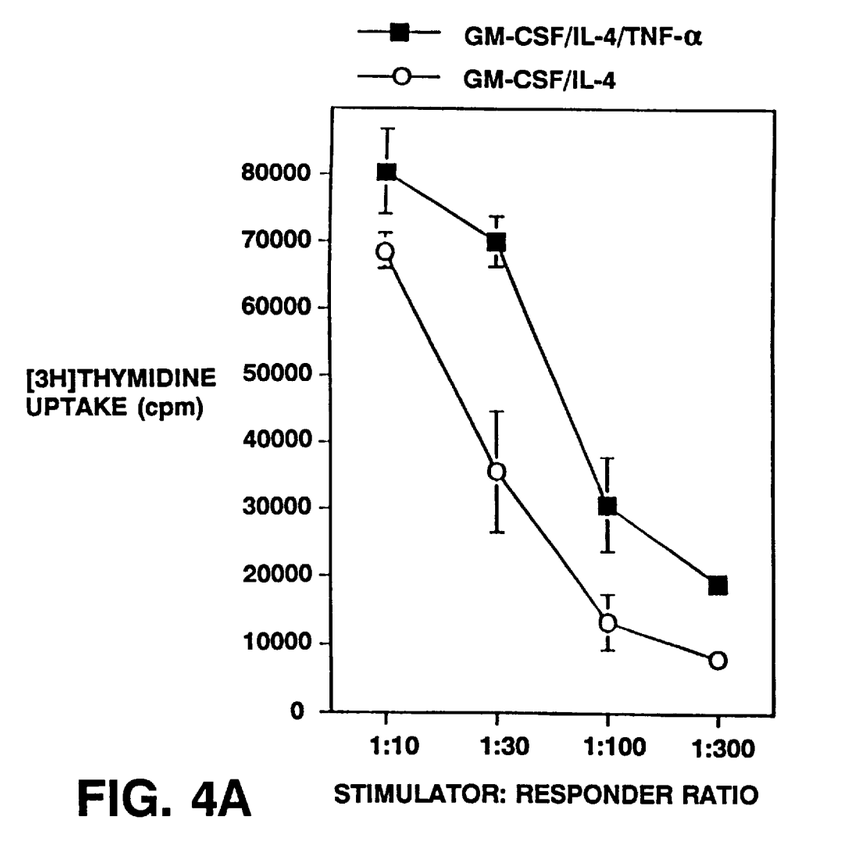
FIGS. 4A–B are a series of graphs showing that monocyte-derived $CD83^+$ cells are potent stimulator cells in an allogeneic mixed leukocyte reaction (AMLR).
Figure 4B:
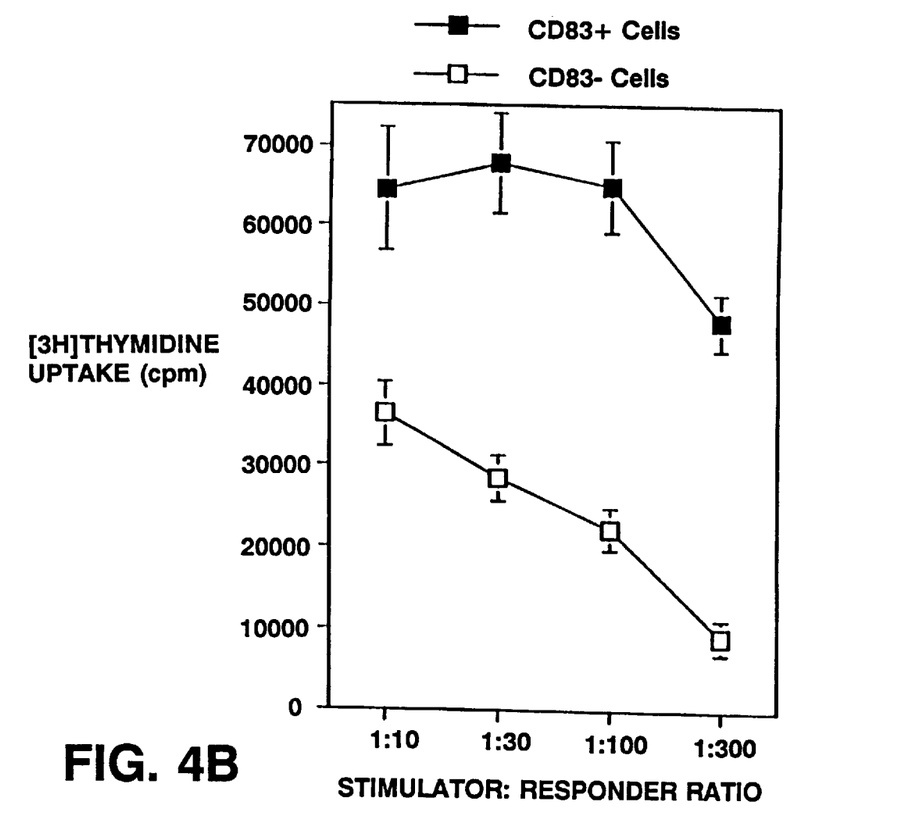

As shown in FIG. 4A, monocytes cultured with GM-CSF, IL-4, and TNF-α induced significantly (p<0.02, paired Student's t test) more proliferation of allogeneic T cells than monocytes cultured with GM-CSF and IL-4. Furthermore, as shown in FIG. 4B, CD83⁺ cells from the GM-CSF, IL-4, and TNF-α cultures initiated significantly higher (p<0.002) stimulatory effects when compared with CD83⁻ cells from the same culture, even at a 1:300 (stimulator:responder) ratio (FIG. 4B). The potent T cell stimulatory activity of monocyte-derived CD83⁺ cells was comparable with that of CD83⁺ blood dendritic cells. These functional results further with all of the characteristics of dendritic cells. As shown in FIGS. 1A–C, monocyte-derived CD83⁺ cells were generated by culturing the cells with GM-CSF, IL-4 and TNF-α. Second, as shown in FIGS. 2A–H, monocyte-derived CD83⁺ cells had a unique cellular morphology characteristic of dendritic cells. Third, as shown in FIG. 3, monocyte-derived CD83⁺ cells displayed a cell surface phenotype similar to that of dermal dendritic cells. Fourth, as shown in FIGS. 4A–B, monocyte-derived CD83⁺ cells were potent stimulator cells in an allogeneic mixed leukocyte reaction. Finally, since the majority of CD14⁺ monocytes represented CD83⁺ cell precursors, at least a subpopulation of CD83⁺ dendritic cells in vivo may differentiate from human blood monocytes.

The combination of GM-CSF, IL-4, and TNF-α was the minimum combination of cytokines necessary for inducing monocyte differentiation into CD83⁺ dendritic cells (FIGS. 1A–C). TNF-α was essential since the monocytes became macrophage-like cells in its absence. However, TNF-α induced optimal monocyte maturation into CD83⁺ dendritic cells when added to monocytes previously cultured with GM-CSF and IL-4 for 5 days (FIG. 1B).

The results of these studies also demonstrated that functionally mature dendritic cells can be derived directly from blood monocytes under the influence of cytokines. Monocyte differentiation into functionally mature dendritic cells, e.g., CD83$^+$ dendritic cells, can be divided into several stages. First, an intermediate maturation stage is induced by GM-CSF and IL-4 where the cells were CD14$^+$ (FIGS. 1A–B) and expressed CD1a at high levels. During the second stage, the presence of TNF-$\alpha$ induced the majority of cells to differentiate into CD83$^+$, CD14$^-$, CD4$^+$ cells with a dendritic morphology. Continued culture of monocyte-derived CD83$^+$ cells led to decreased CD1a expression (FIG. 1C), and acquisition of a dermal dendritic cell phenotype (FIG. 3, Table I). Three populations of dermal dendritic cells have been identified as CD14$^+$/CD1a$^-$, CD14$^-$/CD1a$^+$ and CD14$^-$/CD1a$^-$, each with increasing antigen presenting capacity. Consistent with this, the majority of monocyte-derived CD83$^+$ dendritic cells expressed CD45RO and a subpopulation were CD5$^+$ (FIG. 3). Thus, monocytes may leave the blood, encounter the appropriate cytokines at sites of inflammation and differentiate into dendritic (Langerhans) cells. These cells may also enter the circulation as precursor cells which subsequently differentiate into mature functional antigen presenting cells after a period of in vitro incubation or maturation in vivo.

Media

The invention provides a media containing, but not limited to, GM-CSF, IL-4, and TNF-$\alpha$ that is useful for stimulating the differentiation of monocytes into dendritic cells. While such media generally does not require the use of serum (e.g., fetal bovine serum, calf serum, horse serum, normal mouse serum, human serum, porcine serum, and rabbit serum) those skilled in the art will understand and recognize that serum can be added if desired. Media formulations are generally prepared according to conventional methods. For example, any standard medium including, but not limited to, RMPI-1630 Medium, CMRL Medium, Dulbecco's Modified Eagle Medium (D-MEM), Fischer's Medium, Iscove's Modified Dulbecco's Medium, McCoy's Medium, Minimum Essential Medium, and NCTC Medium can be formulated with GM-CSF, IL-4, and TNF-$\alpha$ at the desired effective concentrations, e.g., the inclusion of GM-CSF (800 U/ml), IL-4 (500 U/ml), and TNF-$\alpha$ (100 U/ml) in the culture media resulted in significant yields of functionally mature monocyte-derived CD83$^+$ dendritic cells. In any event, it will be readily understood that these cytokines are used at sufficient concentrations and are added at appropriate time periods which are effective in increasing the proportion of dendritic cells present in the culture, i.e., by enhancing the differentiation of monocytes into dendritic cells. The amount of cytokines and the time period for the addition of such cytokines, e.g., the addition of TNF-$\alpha$ to a culture medium which includes GM-CSF and IL-4, may be determined and evaluated according to standard methods, e.g., those methods described herein. If desired, media supplements, e.g., salt solutions (e.g., Hank's Balanced Salt Solution or Earle's Balanced Salt Solution), antibiotics, nucleic acids, amino acids, carbohydrates, and vitamins are added according to conventional methods. Standard methods enable the identification of monocyte-derived dendritic cells which are obtained through the use of the culture systems described herein.

The media is useful for a variety of culture conditions and for a variety of biological applications. Examples of such culture conditions include, without limitation, bioreactors (e.g., continuous or hollow fiber bioreactors), cell-suspension cultures, semisolid cultures, and liquid cultures. In addition, the media is useful for a variety of industrial applications. Examples of such biological applications include, without limitation, in vitro dendritic cell culture for human ex vivo therapy and methods for promoting the differentiation of monocytes into dendritic cells in vivo.

For example, the media finds use in the in vitro culture of dendritic cells, including dendritic cells obtained from a human patient. In one working example, monocytes are isolated from virtually any tissue or organ, including, but not limited to, spleen, bone marrow, blood, and liver, according to conventional methods. Alternative standard approaches, alone or in combination, are then used to purify further the monocytes, e.g., through the use of elutriation, plastic adherence, and density gradient centrifugation. These monocytes provide the starting material for producing mature dendritic cells in vitro when treated and cultured according to the methods described herein. For example, the monocytes are cultured in the presence of between about 125–2,000 U/ml of GM-CSF, 1–500 U/ml of IL-4, and 50–50,000 U/ml of TNF-$\alpha$. More preferably, monocytes are cultured in the presence of GM-CSF at a concentration of between about 500–1000 U/ml, in the presence of IL-4 at a concentration of about 250–500, and in the presence of TNF-$\alpha$ at a concentration of 100–1,000 U/ml. Most preferably, cells are cultured in the presence of GM-CSF at a concentration of about 800 U/ml, in the presence of IL-4 at a concentration of about 500 U/ml, and in the presence of TNF-$\alpha$ at a concentration of 100 U/ml. If desired, monocytes can first be cultured in the presence of GM-CSF and IL-4 and then after a sufficient period of time (e.g., 5 days) TNF-$\alpha$ is added to the culture media. The dosages for the addition of the cytokines to the culture media is as described above. Cultures are subsequently incubated under standard tissue culture conditions of temperature, humidity, and pH until an enriched population of dendritic cells is obtained. The enriched population of dendritic cells is subsequently harvested according to conventional methods. Monocyte-derived dendritic cells are then identified according to a variety of conventional techniques, including, but not limited to, the analysis of cellular morphology, detection of cell type specific antigens with monoclonal antibodies (e.g., CD83$^+$), and assaying mixed leukocyte reactions.

Once purified, monocyte-derived dendritic cells can, if desired, be injected by any standard method into the patient. Preferably, the monocyte-derived dendritic cells are injected back into the same patient from whom the source monocytes were obtained. The injection site may be subcutaneous, intraperitoneal, intramuscular, intradermal, or intravenous. The number of dendritic cells injected into the patient in need of treatment is according to standard protocols, e.g., $1 \times 10^4$ to $10 \times 10^6$ cells are injected back into the individual. The number of dendritic cells used for treating any of the disorders described herein varies depending upon the manner of administration, the age and the body weight of the subject, and the condition of the subject to be treated, and ultimately will be decided by the attending physician.

Use

The methods and media compositions described herein are useful for the culture and production of dendritic cells in vitro and in vivo. Given the capacity of dendritic cells to elicit strong antigen-specific helper and cytotoxic T cell responses, the ability to generate large numbers of homogeneous preparations of dendritic cells (e.g., CD83$^+$ dendritic cells) facilitates the manipulation of these cells for the development of a variety of therapies, including without limitation, ex vivo and in vivo human therapies.

The invention therefore encompasses the use of dendritic cells produced according to the methods of the invention for any number of human or veterinary therapeutics. For example, dendritic cells produced as described herein can be used in ex vivo cell transplantation therapies for the treatment of a variety of human diseases, e.g., disorders of the immune system, ranging from rheumatoid arthritis, insulin-dependent diabetes, and multiple sclerosis to acquired immunodeficiency syndrome (AIDS). Accordingly, such cells are useful for modulating autoimmunity and limiting a variety of autoimmune diseases.

In addition, dendritic cells find use in preventing or reducing the likelihood or severity of organ transplant rejection or cancer. For example, dendritic cells pulsed with a lymphoma idiotype immunoglobin or with sonicated mastocytoma cell line P815 which are subsequently transplanted into a patient are capable of providing protection against tumor development. Furthermore, infusions of dendritic cells pulsed with lymphoma-specific idiotype are useful for reducing tumor affliction in a human patient.

Dendritic cells also find use in the ex vivo expansion of T cells, e.g., $CD4^+$ cells or $CD8^+$ cells or both. Thus, such dendritic cells are useful for stimulating the proliferation and reconstitution of $CD4^+$ cells or $CD8^+$ cells or both in a human having an immune disorder. Reconstitution of the immune system, e.g., a patient's $CD4^+$ cells, is useful in immunotherapy for preventing, suppressing, or inhibiting a broad range of immunological disorders, e.g., as found during HIV infection. Treatment involving the use of dendritic cells is generally useful for treating or delaying additional immunological or clinical deterioration.

The dendritic cells described herein are also useful for vaccine development. For example, administration of antigens to dendritic cells facilitate the use of these cells for active immunization in situ.

In addition, dendritic cells are useful for the generation of antibodies (e.g., monoclonal antibodies) that recognize dendritic cell-specific markers. Anti-dendritic cell antibodies are produced according to standard hybridoma technology (see, e.g. Kohler et al., Nature, 256:495, 1975; Kohler et al., Eur. J. Immunol. 6:511, 1976; Kohler et al., Eur. J. Immunol., 6:292, 1976; Hammerling et al., In Monoclonal Antibodies and T Cell Hybridomas, Elsevier, N.Y., 1981). Such antibodies are useful for the evaluation and diagnosis of a variety of immunological disorders, e.g., psoriasis. Furthermore, monoclonal antibodies which are specific for an epitope found on a dendritic cell are useful for purifying a population of such cells according to a wide-variety of conventional methods.

Dendritic cells are also useful for preparing antigen-activated dendritic cells according to standard methods in which antigen-activated dendritic cells have been exposed to antigen and express modified antigens for presentation to and activation of T cells. Antigen-activated dendritic cells are generally produced by exposing antigen, in vitro, to the dendritic cells prepared according to the methods described herein. Dendritic cells are then plated in culture dishes and exposed to antigen in a sufficient amount and for a sufficient period of time to allow the antigen to bind to the dendritic cells. The amount of antigen and time necessary to achieve binding of the antigen to the dendritic cells may be determined according to any conventional technique, e.g., an immunoassay.

Pharmaceutical compositions including, but not limited to, the combination of cytokines described herein may be conveniently administered to promote the differentiation of monocytes into dendritic cells in vivo. Ordinarily, the therapeutic composition will be administered at a dosage effective to stimulate differentiation of a monocyte into a dendritic cell. Preferable routes of administration include, for example, subcutaneous, intravenous, intraperitoneally, intramuscular, transdermal or intradermal injections which provide continuous, sustained levels of cytokines in the patient. In other preferred routes of administration, the cytokines can be given to a patient by injection or implantation of a slow release preparation, for example, in a slowly dissociating polymeric or crystalline form; this sort of sustained administration can follow an initial delivery of the drug by more conventional routes (for example, those described above). Alternatively, the cytokines can be administered using an external or implantable infusion pump, thus allowing a precise degree of control over the rate of drug release. Note that continuous administration using a subcutaneous infusion pump may be desirable when the compounds to be used have a rather short half-life or lacks long-lasting activity. Conversely, single or intermittent administration is acceptable or even preferable when the compounds to be used have a long half-life or long-lasting activity. Treatment of human patients will be carried out using in vivo administration of a therapeutically effective amount of GM-CSF, IL-4, and TNF-α. Suitable carriers and their formulation are described for example in Remington's Pharmaceutical Sciences by E. W. Martin (supra). The amount of GM-CSF, IL-4, and TNF-α to be administered varies depending upon the manner of administration, the age and body weight of the patient, and with the type of disease, extensiveness of the disease or the treatment rendered, and size of the patient. Generally amounts will be in the range of those described herein. For example, GM-CSF, IL-4, and TNF-α are generally administered, at a dosage that promotes the differentiation of a monocyte into a dendritic cell, typically in the range of 800 U/ml, 500 U/ml, and 100 U/ml for GM-CSF, IL-4, and TNF-α, respectively. Such an amount of the active compounds as determined by the attending physician is referred to herein as a "therapeutically effective amount." Treatment is started generally with the diagnosis or suspicion of a disease, e.g., an immune disorder such as diabetes, and is generally repeated on a daily basis. The efficacy of the treatment or protection regimens is assessed with standard methods of monitoring or diagnosing patients for any of the disorders described herein.

The methods of the invention may be used to reduce the disorders described herein in any mammal, for example, humans, domestic pets, or livestock. Where a non-human mammal is treated, the combination of cytokines described herein or the dendritic cells employed are preferably but not necessarily specific for that species.

All publications and patents mentioned in this specification are herein incorporated by reference to the same extent as if each individual publication or patent was specifically and individually indicated to be incorporated by reference.

Other Embodiments

From the foregoing description, it will be apparent that variations and modifications may be made to the invention described herein to adapt it to various usages and conditions. Such embodiments are also within the scope of the following claims.

We claim:

1. A method for inducing the differentiation of a population of monocytes into a population of cells comprising greater than 50% mature $CD83^+$ dendritic cells, said method comprising culturing said monocytes in an induction medium comprising granulocyte/macrophage-colony stimulating factor ("GM-CSF"), interleukin-4 ("IL-4"), and tumor necrosis factor-α ("TNF-α"), said GM-CSF, IL-4, and TNF-α being present simultaneously in said induction medium in sufficient amounts to induce said differentiation, said culturing resulting in said induction of differentiation.

2. The method of claim 1, comprising first culturing said monocytes in a medium comprising GM-CSF and IL-4, and then adding TNF-α to said GM-CSF and IL-4 medium.

3. The method of claim 1, wherein said monocytes are human blood monocytes.

4. The method of claim 3, wherein said human blood monocytes are CD14$^+$ and CD1a$^-$.

5. The method of claim 3, wherein said human blood monocytes are plastic-adherent monocytes.

6. The method of claim 1, wherein said dendritic cells are human dendritic cells.

7. The method of claim 6, wherein said human dendritic cells induce T cell proliferation.

8. The method of claim 1, comprising maintaining GM-CSF concentration in said medium in the range of about 125–2,000 U/ml, IL-4 concentration in the range of about 1–500 U/ml, and TNF-α concentration in the range of about 50–50,000 U/ml.

9. The method of claim 1, further comprising administering said dendritic cells to a mammal.

10. The method of claim 1, wherein said population of dendritic cells is not substantially derived by proliferation of dendritic cells.

11. A method for generating a population of greater than 50% mature CD83$^+$ dendritic cells, said method comprising:
   (a) inducing the differentiation of a population of monocytes into said population of dendritic cells, by culturing said population of monocytes in an induction medium comprising granulocyte/macrophage-colony stimulating factor ("GM-CSF"), interleukin-4 ("IL-4"), and tumor necrosis factor-α ("TNF-α"), said GM-CSF, IL-4, and TNF-α being simultaneously present in said induction medium in sufficient amounts to induce said differentiation; and
   (b) recovering said population of said dendritic cells.

12. The method of claim 11, comprising first culturing said population of monocytes in a medium comprising GM-CSF and IL-4, and then adding TNF-α to said GM-CSF and IL-4 medium.

13. The method of claim 12, wherein said TNF-α is added to a medium containing said GM-CSF and IL-4 after culturing said cells for a period of about 5 days.

14. The method of claim 13, wherein said human blood monocytes are CD14$^+$ and CD1a$^-$.

15. The method of claim 14, wherein said human blood monocytes are plastic-adherent monocytes.

16. The method of claim 11, wherein said population of monocytes are human blood monocytes.

17. The method of claim 11, wherein said population of dendritic cells are human dendritic cells.

18. The method of claim 17, wherein recovery of said population of dendritic cells includes flow cytometry.

19. The method of claim 17, wherein recovery of said population of dendritic cells includes cell sorting.

20. The method of claim 11, comprising maintaining GM-CSF concentration in said medium in the range of about 125–2,000 U/ml, IL-4 concentration in the range of about 1–500 U/ml, and TNF-α concentration in the range of about 50–50,000 U/ml.

21. The method of claim 20, comprising first culturing said population of monocytes in an initial medium comprising GM-CSF and IL-4 and then adding TNF-α to said initial medium.

22. The method of claim 11, wherein said population of dendritic cells is not substantially derived by proliferation of dendritic cells.

* * * * *